United States Patent [19]

Wiley et al.

[11] Patent Number: 5,033,480
[45] Date of Patent: Jul. 23, 1991

[54] SHORT SELF ADHESIVE DENTURE GUARD

[76] Inventors: Christopher W. Wiley, 1451 Green River Rd.; Peter T. Esposito, 118 Cobbleview Rd., both of Williamstown, Mass. 01267

[21] Appl. No.: 497,647

[22] Filed: Mar. 23, 1990

[51] Int. Cl.⁵ ................................................ A61C 5/14
[52] U.S. Cl. .................................................... 128/861
[58] Field of Search ............... 128/859, 860, 861, 862, 128/858, 10; 433/6

[56] References Cited

U.S. PATENT DOCUMENTS

| | | | |
|---|---|---|---|
| 2,705,492 | 4/1955 | Chandler | 128/862 |
| 2,706,478 | 4/1955 | Porter | 128/862 |
| 3,016,052 | 1/1962 | Zubren | 213/89 |
| 3,236,235 | 2/1966 | Jacobs | 128/861 |
| 3,333,582 | 8/1967 | Cathcart | 128/862 |
| 3,513,838 | 5/1970 | Foderick et al. | 128/861 |
| 3,864,832 | 2/1975 | Carlson | 128/862 |
| 4,063,552 | 12/1977 | Going et al. | 128/861 |
| 4,350,154 | 9/1982 | Feldbau | 128/861 |

Primary Examiner—Robert A. Hafer
Assistant Examiner—Michael Brown
Attorney, Agent, or Firm—Arthur K. Hooks

[57] ABSTRACT

A dental guard fittable over a patient's upper incisors is composed of an arcuate plastic tray of about 1.5 inches in length and having in cross-section a U-shape. A compliant elastomeric adhesive plug of a hydrogel lies within and is self-adhered to the channel of the U-shaped tray so that when pressed into place over the patient's incisors, the teeth remain embedded in the plug and the dental guard remains adhered in position over the incisors but leaves the posterior teeth (molars including premolars) on either side uncovered. The use of such a dental guard protects the incisors from the levering forces exerted by the laryngoscope blade during intubation and provides the intubator an unobstructed view for easily guiding an endotracheal tube via the pharynx through the vocal cords and into the trachea.

7 Claims, 1 Drawing Sheet

SHORT SELF ADHESIVE DENTURE GUARD

BACKGROUND OF THE INVENTION

This invention relates to tooth protectors and more particularly to dental guards for protecting the incisors of a patient undergoing medical procedures such an laryngoscopy, endotracheal intubation, and/or anesthesia.

Many tooth protecting devices have been devised for use during medical procedures and for athletic purposes. Each protector is comprised of an arcuate tray having in cross-section a U-shape and having in top view a horse-shoe shape. The arcuate or horse-shoe tray has a curvature (seen in the top view) that bends through not quite a 180 degree angle of arc to conform to the curvature of the upper or lower row of teeth of the person to be protected. The U-chaped channel or trough of the tray in some prior art tooth protectors is made great enough that the protector will be usable by essentially all adult and even adolescent patients representing a wide range of human dental geometries. Such universal-sized tooth protectors, however, must be extra-long and the channel widths quite wide and bulky at the tray ends because of the large variation in dental arch forms from person to person. Prior art tooth guards are often used in pairs: one for protecting the entire upper row of teeth, and the other for the lower row.

Especially because of this full arch design, prior art tooth guards have been cumbersome for medical personnel to insert, and during intubation have obstructed the view of the vocal cords, have interfered with the endotracheal tube placement, and frequently lacked the retentiveness to remain firmly in place during the procedure. For these reasons none of the prior art has obtained significant use for medical procedures even though damaged upper incisor teeth remains the most prevalent complication and source of damage claims for the aforementioned medical procedures.

Endotracheal intubation is a procedure normally performed by trained medical professionals, whereby a tube is inserted via the mouth into the trachea of a patient to allow mechanical ventilation of the lungs, suction of secretions from the bronchial passages, and administration of oxygen during general anesthesia for surgery because of serious illness, cardiac arrest, or coma. This tube is called an endotracheal tube, and its purpose is to act as a conduit for oxygen and/or anesthetic gases into the trachea. Placement of the endotracheal tube requires direct visualization of the vocal cords through which the tube must pass. Visualization of the vocal cords is accomplished by using a laryngoscope which consists of a handle, a blade extending at a right angle to the handle, and a light source at the end of the blade. The blade is inserted into the patient's mouth and extends back to the patient's soft palate and epiglottis. The light source at the tip of the blade illuminates these structures. Lifting the laryngoscope handle causes the blade to elevate the soft palate and epiglottis thereby exposing the vocal cords so that the endotracheal tube may be inserted through them. This lifting motion of the handle is often accompanied by a pivoting which places the proximal portion of the blade into direct contact with the delicate cutting edge of the upper incisors. This may result in considerable forces being applied by the laryngoscope blade to the upper incisors which can easily result in damage such as chipping or complete fracture.

A primary object of this invention is to provide an improved dental guard which is easily inserted by medical personnel and which better protects a patient's teeth against damage during intubation while at the same time allowing an unobstructed view and path of insertion for the endotracheal tube.

A further object of this invention is to provide a short dental guard for protecting the upper incisors of the patient without covering the molars toward providing larger channels of visibility and access.

SUMMARY OF THE INVENTION

Each dental guard is comprised of an arcuate channel member or tray having a flattened U-shape in cross-section. This arcuate tray is intended to be placed over just the anterior upper teeth (incisors and canines), and preferably just over the incisors, of a patient to be intubated. It is therefore substantially shorter than necessary to cover all the upper (or lower) teeth. It preferably has a length, taken along the tray arc, of about 1.5 inches (3.75 cm) roughly corresponding to the separation between the pair of upper canine teeth. Also, in order to conform to the curvature of a person's upper incisors and canines only, the curvature of the dental guard should amount to less than 140 degrees of arc.

It will be particularly advantageous in the small dental guard of this invention that the channel of the tray be filled by an elongated plug of a non-toxic permanently deformable and elastomeric adhesive which is contained within and adhered to the channel of the tray. This plug is preferably a non-toxic hydrogel. When the dental guard is pressed in place over a patient's upper incisors, the compliant adhesive plug will be deformed to take the shape of and conform to the teeth as well as adhere to them, and will thereafter still remain somewhat elastomeric. This adhesion feature is particularly important in this dental guard design, which does not extend over all of the upper teeth, but must depend for adhesion on the front upper incisors and possibly the canine teeth only.

Furthermore, since the range of variation among humans in the distance between upper canines is relatively small, a universal-sized guard of this invention, designed to fit essentially all adults and adolescents, may be made to fit better and be less obtrusive than the much larger and bulkier tooth protectors of the prior art.

This invention recognizes that for protecting the front upper teeth during endotracheal intubation it is not necessary to employ conventionally large tooth protectors of horse-shoe shape covering all of the teeth. The provision of a small dental guard covering essentially only the upper anterior teeth provides a device substantially less cumbersome to insert while also providing an unobstructed view and path for inserting the endotracheal tube between the patient's right or left molars.

DESCRIPTION OF THE PREFERRED EMBODIMENTS

Figure 1:
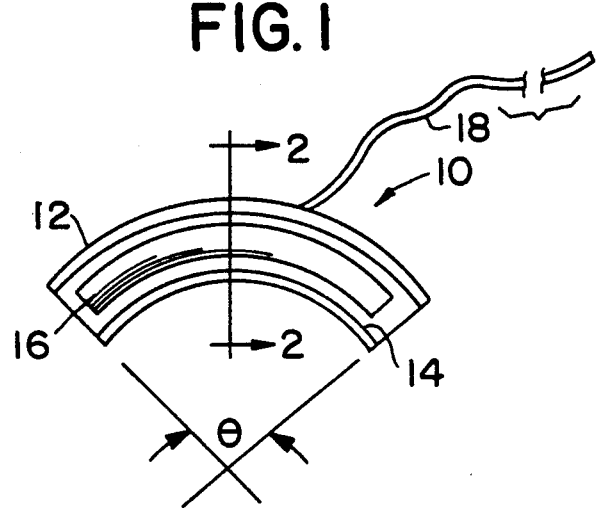
FIG. 1 shows in top view a denture guard of this invention.
Figure 2:
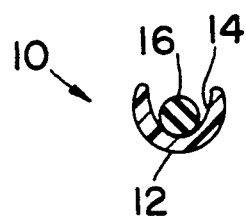
FIG. 2 shows in cross-sectional view the denture guard of FIG. 1 taken in section 2—2.

Referring to FIGS. 1 and 2, a dental guard 10 is comprised of the arcuate tray having everywhere along its length a cross-section geometry that is U-shaped, as is exemplified by the section 2—2 illustrated in FIG. 2. The tray 12 is made of a thermoplastic material such as polypropylene or any other mechanically strong material including thermosetting plastics and some fiber-reinforced materials providing they are not toxic.

The U-shaped feature of the tray 12 provides a trough or channel 14 in which and to which is adhered an elongated plug 16 of a compliant adhesive material, i.e. a material that is an adhesive and both elastomeric and permanently deformable. In this embodiment, plug 16 is a hydrogel, e.g. part number RG-60X made by Promeon Division of Medtronic, Inc. of Brooklyn Center, N.Y.

Firmly attached to the front (top as shown in FIG. 1) outside surface of the tray 12 is a string 18. This string may be attached at the time of forming the tray by partial embedment therein, for example at the step of molding the tray. String 18 is to be used as a safety device. The dental guard of this invention is small enough in relation to the throat that there exists a potential danger that it may be inhaled or swallowed by the patient. The distal end of the string 18 may be taped to the patient's face, pinned to their gown, or otherwise anchored to preempt that danger and allow easy immediate retrieval of the device if needed. Even were it not so anchored, it will hang out of the patient's mouth serving as a flag or indicator that the dental guard, normally hidden behind the patient's upper lip, is present. It should be noted however, that the likelihood of the dental guard coming loose after having been properly seated over the teeth is remote because of the excellent adhesion provided by the hydrogel plug 16.

Figure 3:
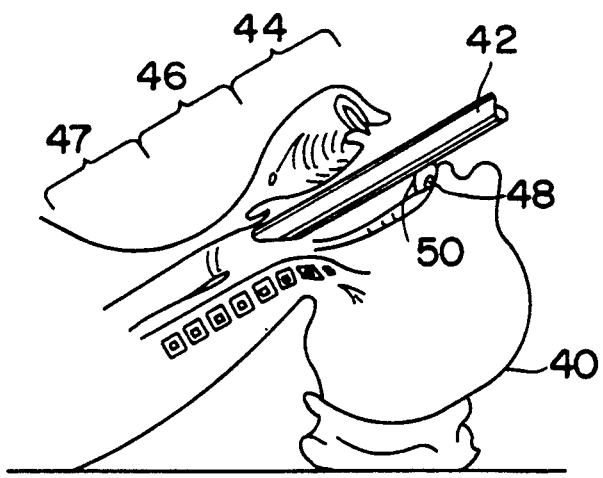
FIG. 3 shows in side-sectional view a patient with a laryngoscope inserted in preparation for intubation.

The method for intubating a comatose or anesthetized patient begins by pressing one of the above-described dental guards over the patient's upper incisors until firmly seated. The supine patient's head is tipped back, extending the neck, and providing a straight course through the mouth to the larynx. A pillow or roll under the head and/or neck holds and stabilizes the head 40 (FIG. 3) while the intubator, standing behind the patient, inserts the laryngoscope 42 into the mouth 44 and on into the pharynx 46.

The laryngoscope is inserted into the right side of the mouth and directed down to the back of the throat. The patient's tongue is swept by the laryngoscope blade toward the left side of the patient's mouth, leaving an aperture between the blade and the right corner of the mouth and between the upper and lower right molars. The light at the end of the laryngoscope blade illuminates the epiglottis which is then lifted by the tip of the laryngoscope blade allowing the vocal cords to be directly seen. At this point an endotracheal tube (not shown) is passed through the right corner of the mouth and threaded beside the blade and through the vocal cords into the trachea. That laryngoscope is then removed and the endotracheal tube fixed in position using tape.

The insertion of the laryngoscope into the right side of the mouth and sweeping the tongue to the left side to look between the patient's right molars etc. is standard practice, but to reverse the sides in this procedure also constitutes acceptable practice.

Lifting the epiglottis to expose the vocal cords often entails prying against the upper incisors 48 which are protected by the dental guard 50. In addition, after removal of the endotracheal tube and upon awakening from the general anesthesic, patients may bite down or clench their teeth with such force as to damage the upper incisors. The continued presence of the dental guard throughout the anesthetic until the patient is wide awake will prevent this. Thus the need for secure adherence of the dental guard 50 is evident.

What is claimed is:

1. A dental guard to be pressed onto a patient's upper incisors to prevent breaking and chipping these teeth by a laryngoscope during and after preparation for insertion of an endotracheal tube via the mouth into the trachea, said dental guard comprising:
    a) a short trough-like arcuate tray having a cross-section of U-shape, said tray having a length, taken along the tray arc, about equal to the arcuate length of the row of upper incisors of an adult human; and
    b) an elongated plug of a permanently deformable and elastomeric adhesive, capable of deforming to take the shape of and adhering to the patient's upper incisors and lying within and being self-adhered to the channel of said trough-like tray.

2. The dental guard of claim 1 wherein a string has one end firmly attached to said tray, for protruding from the patient's mouth to indicate the presence of the dental guard and for being anchored outside the mouth to prevent the dental guard from being swallowed or inhaled.

3. The dental guard of claim 1 wherein the curvature over the entire length of said arcuate tray amounts to an arc of less than 140 degrees.

4. The dental guard of claim 1 wherein the depth of said trough-like tray is no greater than that which is generally needed to just cover the adult patient's front upper teeth and is less than 0.75 inch (1.9 cm).

5. The dental guard of claim 1 wherein said length of said tray is about 1.5 inches (3.8 cm).

6. The dental guard of claim 1 wherein said elongated adhesive plug is a hydrogel.

7. A method for intubating a patient to allow externally controlled mechanical ventilation comprising:
    a) providing a dental guard which includes a short trough-like arcuate tray and an elongated plug of a compliant adhesive lying within and self-adhered to the channel of said trough-like tray, said tray having a length, taken along the tray arc, about equal to the arcuate length of the row of upper incisors of an adult human;
    b) pressing said dental guard onto a patient's front upper incisors to force the patient's incisors into said plug of compliant adhesive and to adhere said dental guard to said patient's upper incisors;
    c) tipping said patient's head back and inserting the distal end of a laryngoscope into the patient's mouth;
    d) advancing said distal end further into the patient's pharynx, and visualizing and elevating the epiglottis to expose the vocal cords with said denture-guard protecting the incisors from the proximal end of said laryngoscope; and
    e) inserting an endotracheal tube into a side of the patient's mouth, along the laryngoscope blade, and through the vocal cords into the trachea, all the while being guided by looking through the gap between the patient's bare molars.

* * * * *